US008629289B2

(12) United States Patent
King et al.

(10) Patent No.: US 8,629,289 B2
(45) Date of Patent: Jan. 14, 2014

(54) METHOD FOR THE PREPARATION OF 1-ACETYL-6-AMINO-3,3-DIMETHYL-2,3-DIHYDROINDOLE

(75) Inventors: Anthony King, Morristown, NJ (US); Robert Larsen, Newbury Park, CA (US); Tj Li, Thousand Oaks, CA (US); Yuelie Lu, Shanghai (CN)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/140,002

(22) PCT Filed: Dec. 18, 2009

(86) PCT No.: PCT/US2009/068798
§ 371 (c)(1),
(2), (4) Date: Feb. 6, 2012

(87) PCT Pub. No.: WO2010/071828
PCT Pub. Date: Jun. 24, 2010

(65) Prior Publication Data
US 2012/0136163 A1  May 31, 2012

Related U.S. Application Data

(60) Provisional application No. 61/139,152, filed on Dec. 19, 2008.

(51) Int. Cl.
C07D 209/04 (2006.01)

(52) U.S. Cl.
USPC ............................................. 548/508

(58) Field of Classification Search
None
See application file for complete search history.

(56) References Cited

U.S. PATENT DOCUMENTS 6,977,304 B2   12/2005  Wurziger et al.
2003/0181733 A1*  9/2003  Wurziger et al. ........... 548/508

FOREIGN PATENT DOCUMENTS

WO    WO 01/92225      12/2001
WO    WO 2006/119504   11/2006

OTHER PUBLICATIONS

Edwards, JP et al., "New Nonsteroidal Androgen Receptor Modulators Based on 4-(Trifluoromethyl)-2(1H)-Pyrrolidino[3,2-g]Quinolinone," *Bioorganic & Medicinal Chemistry Lettes*, 8: 745-750 (1998).
Grammaticakis, P. "Mid-ultraviolet absorption spectra and some methods of formation of some indole and indilenine derivatives," *Compt. Rend.* 210: 569-572 (1940).
Kanaoka, Y. et al. "Fischer Indole Synthesis and Ethylation of 2,3-Disubstituted Indoles with Polyphosphate Esters," *Chemistry and Industry*, 11, p. 473 (Mar. 13, 1965).
Liu, KG et al. "Rearrangement of 3,3-Disubstituted Indolenines and Synthesis of 2,3-Substituted Indoles," *Organic Letters*, 8(25): 5679-5771 (2006).
Edwards, JP et al., "New Nonsteroidal Androgen Receptor Modulators Based on 4-Trifluoromethyl)-2(1H)-Pyrrolidino[3,2-g]Quinolinone,"*Bioorganic & Medicinal Chemistry Lettes*, 8: 745-750 (1998).
Grammaticakis, P. "Mid-ultraviolet absorption spectra and some methods of formation of some indole and indilenine derivatives,"*Compt. Rend.* 210: 569-572 (1940).
International Search Report for PCT/US2009/066798, dated Jul. 1, 2010.
Kanaoka, Y. et al. "Fischer Indole Synthesis and Ethylation of 2,3-Disubstituted indoles with Polyphosphate Esters,"*Chemistry and Industry*, p. 473 (Mar. 13, 1965).
Liu, KG et al. "Rearrangement of 3,3-Disubstituted Indoienines and Synthesis of 2,3-Substituted Indoles,"*Organic Letters*, 8(25): 5679-5771 (2006).

* cited by examiner

*Primary Examiner* — Nyeemah A Grazier
(74) *Attorney, Agent, or Firm* — Finnegan, Henderson, Farabow, Garrett & Dunner, LLP

(57) ABSTRACT

The present invention relates to processes for preparing indoline derivatives, particularly 1-acetyl-6-amino-3,3-dimethyl-2,3-dihydroindole.

19 Claims, No Drawings

METHOD FOR THE PREPARATION OF 1-ACETYL-6-AMINO-3,3-DIMETHYL-2,3-DIHYDROINDOLE

CROSS REFERENCES TO RELATED APPLICATIONS

This application claims the benefit of U.S. Provisional Application No. 61/139,152, filed on Dec. 19, 2008, of which is hereby incorporated by reference in its entirety and for all purposes as if specifically and fully set forth herein.

FIELD OF THE INVENTION

The present invention relates to processes for preparing indoline derivatives, particularly 1-acetyl-6-amino-3,3-dimethyl-2,3-dihydroindole.

BACKGROUND OF THE INVENTION

Indole derivatives have been and continue to be important intermediates for dyestuffs and pharmaceuticals. Since it's discovery in the 1880's, Emil Fischer's synthetic method has been one of the most widely used methods for preparing indoles from aryl hydrazines. Various catalysts have been used to effect the cyclization of arylhydrazones derived from the reaction of aryl hydrazines and ketones/aldehydes. Bronsted acids including $H_2SO_4$, HCl, PPA, TFA, oxalic acid, formic acid, HI, HBr, propionic acid, and AcOH, Lewis acids including $ZnCl_2$, $ZnBr_2$, $TiCl_4$, $SnCl_2$, CuCl, CuBr, and $PCl_3$, and solid acids including zeolites, and montmorillonite clay, Lewis acidic ionic liquids such as 1-butyl-pyridium chloride.$3AlCl_3$ and choline chloride.$2ZnCl_2$ and Bronsted acidic ionic liquids including $BMImHSO_4$, $BMImH_2PO_4$, HMImTA, $HMImBF_4$, $HMImNO_3$ and HMImOTf, among others, have been used.

However, because of the complex mechanism involved, there exists high variability in the preferred conditions for specific indoles. In other words, one set of reagents and conditions does not work best for all indoles.

U.S. Pat. No. 5,179,211 describes a process of preparing indoles from phenylhydrazine and ketones in the presence of less than 5 equivalents of an acid having a pK of 1.3-4.5 and an aqueous medium. The process preferably is carried out at a temperature of 80-110° C. Preferably 2-4 equivalents of acid are used.

Liu and Robichaud (Tet Lett. 48, 461 (2007)) describe that the use of acetic acid and a temperature of 60° C. gave indolenines in good yield. Elevated temperatures led to significant side products and rearrangements.

Liu et al (Org. Lett, 8, 5769 (2006)) describe that a mixture of AcOH and MsOH also functioned in a reaction with cyclohexanecarbaldehyde and phenylhydrazine whereas $ZnCl_2$ and $H_2SO_4$ did not perform as well. A mixture of HCl in AcOH in a reaction with isobutylaldehyde led to rearrangement to form 2,3-substituted indoles.

Edwards et al (Bio and Med Chem Lett, 8, 745 (1998)) describe the use of Fischer protocol (AcOH, 60° C.), reduction of indoles to indolenines, nitration and hydrogenation to the amino-substituted compounds.

Certain substituted indoline compounds, such as those disclosed in U.S. Pat. No. 6,995,162, including motesanib, have been found to be useful in treating conditions associated with angiogenesis, including the treatment of cancers. In addition, U.S. Pat. No. 6,878,714 describes the method of making 1-acetyl-6-amino-3,3-dimethyl-2,3-dihydroindole using reductive Heck conditions. This route generally involves the palladium-catalyzed cyclization of allylacetamide. Liu et al. (Tet Lett, 48, 2307 (2007)) describe the synthesis of substituted indolines using the Heck cyclization. The use of palladium in such reactions adds an undesired expense that would be advantageous to avoid. Thus, there is an ongoing need for more facile and higher yielding processes for preparing indoline derivatives.

SUMMARY OF THE INVENTION

The present invention is generally directed to processes for preparing indoline derivatives using modified Fischer indole conditions.

In some embodiments, the present invention is directed to processes for preparing indoline compounds, comprising the steps of:

a) reacting

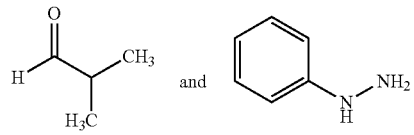

to form a hydrazone;

b) cyclization of the hydrazone in the presence of a Fischer catalyst to form a 3H-indole;

c) reduction of the 3H-indole to form a 2,3-dihydro-indole;

d) nitration of the 2,3-dihydro-indole to form a 6-nitro-2,3-dihydro-indole;

e) acylation of the 6-nitro-2,3-dihydro-indole to form the protected 6-nitro-2,3-dihydro-indole; and f) conversion of the nitro group to form 6-amino-2,3-dihydro-indole.

In other embodiments, the processes further directed to processes for preparing a mixture of hydrazones of the formula

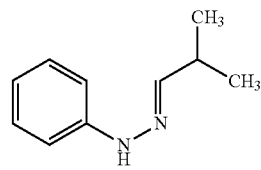

[(E/Z)-1-(2-methylpropylidene)-2-phenylhydrazine].

In other embodiments, the processes further directed to processes for preparing the following compound

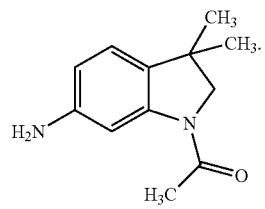

In other embodiments, the invention is directed to a non-aqueous cyclization of a mixture of hydrazones of the formula

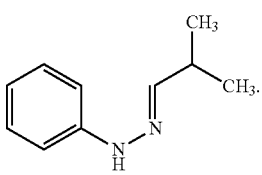

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth. The term "comprising" is meant to be open ended, including the indicated component but not excluding other elements.

The abbreviations in the specification correspond to units of measure, techniques, properties, or compounds as follows: "min" means minutes, "h" means hour(s), "mM" means microliter(s), "mL" means milliliter(s), "mM" means millimolar, "M" means molar, "mmole" means millimole(s), "cm" means centimeters, "SEM" means standard error of the mean and "IU" means International Units.

It is believed the chemical formulas and names used herein correctly and accurately reflect the underlying chemical compounds. However, the nature and value of the present invention does not depend upon the theoretical correctness of these formulas, in whole or in part. Thus it is understood that the formulae used herein, as well as the chemical names attributed to the correspondingly indicated compounds, are not intended to limit the invention in any way, including restricting it to any specific tautomeric form or to any specific optical or geometric isomer.

When ranges are used herein for physical properties, such as molecular weight, or chemical properties, such as chemical formulas, all combinations, and subcombinations of ranges specific embodiments therein are intended to be included.

When any variable occurs more than one time in any constituent or in any formula, its definition in each occurrence is independent of its definition at every other occurrence.

General Procedure

Scheme A

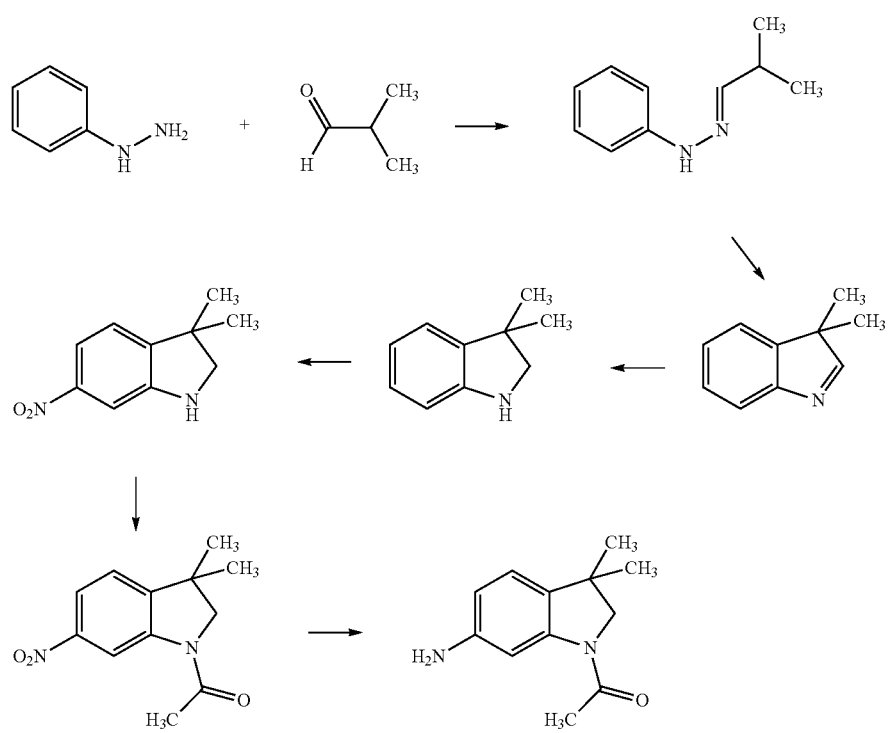

For a review on the Fischer Indole Synthesis, see B. Robinson, Chem. Rev. 1963, 63, 373-401. One method of preparing the desired compounds is shown in Scheme A above.

Formation of the Hydrazone and Cyclization

Embodiments of the process include cyclization of the compound resulting from treatment of isobutyraldehyde with phenylhydrazine.

In the process, it is possible to solubilize the phenylhydrazine first or the aldehyde first or added simultaneously. In certain embodiments of this step of the process, the phenylhydrazine is first diluted in solvent prior to the addition of the aldehyde. In certain embodiments of this step of the process, the phenylhydrazine cooled to a solid prior to the addition of the aldehyde. The invention also relates to a process where an excess of isobutyraldehyde is added to the phenylhydrazine. The invention also relates to a process in an atmosphere where minimal oxygen is present, such as in a nitrogen environment. The process may include hydrazone formation carried out at a temperature range of about 10° C. and about 30° C. Embodiments of the process include a hydrazone formation carried out at a temperature below about 20 to about 25° C.

The present invention also relates to a process where the phenylhydrazone is isolated prior to the cyclization step. The appropriate isolated phenylhydrazone can be cyclized to form the indole as described above by treatment with acid, e.g. methanesulfonic acid.

Alternatively, the hydrazone is not isolated prior to treatment with the acid.

The cyclization with Fischer indole chemistry involves using a Bronsted acid as a catalyst. Suitable acids include trifluoroacetic acid (TFA), acetic acid, toluenesulfonic acid, methanesulfonic acid, difluoroacetic acid and sulfuric acid. The invention also relates to the use of methanesulfonic acid as a catalyst.

Embodiments of the process include acid compounds in an amount of more then 5 equivalents per mole of the hydrazine employed. The invention also relates to the use of about 8 equivalents of acid.

Embodiments of the process include cyclization in a non-aqueous solvent environment. Such solvents include heptane, hexane, toluene, benzene, xylenes, isopropyl alcohol, dioxane, dichloromethane, ethanol, acetonitrile and tetrahydrofuran. Alternatively, some of the catalyst acids could be used neat, without additional solvent, where the acid played the role of solvent too. Such acids include acetic acid and formic acid. The present invention also relates to a process where non-polar solvents are used, e.g. heptane, hexane, toluene, benzene and xylenes. The present invention also relates to a process where a mixture of solvents is utilized. In certain embodiments of the invention, heptane is used as the solvent. Where the term "non-aqueous" is used, it is not to intend that water is not generated by a reaction step.

Embodiments of the process include a cyclization carried out at a temperature of above about $-15°$ C. and the temperature of reflux of the solution. Embodiments of the process include a cyclization carried out at a temperature of above about $-15°$ C. and about $30°$ C. The invention also relates to a cyclization carried out at a temperature of above about room temperature. The invention also relates to a cyclization carried out at a temperature that is above the melting point of the catalyst acid. The invention also relates to a process in an atmosphere where minimal oxygen is present, such as in a nitrogen environment.

Formation of the Indoline

In certain embodiments of this step of the process, the reduction involves the use of a reducing agent that is not water sensitive. For example sodium borohydride, $NaBH(OAc)_3$ and sodium cyanoborohydride are acceptable. In certain embodiments of this step of the process, an excess of reducing agent is used. In certain embodiments of this step of the process, >1 to about 2 equivalents of reducing agent is used. In certain embodiments of this step of the process, about 1.2 to about 1.8 equivalents of reducing agent is used. In certain embodiments of this step of the process, about 1.2 or about 1.8 equivalents of reducing agent is used.

Embodiments of the process include a reduction carried out at a temperature of above about $15°$ C. and about $25°$ C. In certain embodiments of this step of the process, the reaction can be performed at a temperature of about room temperature. Basification can be accomplished with NaOH, ammonium hydroxide or the like.

The indoline can be isolated as a salt by treatment with an acid, such as HCl.

Nitration

Nitration of the dihydro-indole ring such as with $H_2SO_4$ and fuming $HNO_3$ at a temperature below RT, further at a temperature of about $-15°$ C. to about $10°$ C., and preferably at about $0°$ C., gives the 6-nitro-3,3-dimethyl indoline. Other methods of nitration would be acceptable too.

Protection of the Dihydro-Indole

The free amine of the indoline can be protected such as by acetylation. The acetylation can be accomplished such as with acetyl chloride or acetic anhydride, under standard coupling chemistry, such as with DIEA, and DMAP, at a temperature of about RT, in a suitable solvent, such as DCM, DMF and/or DMAC.

Conversion of the Nitro Group to an Amine

The conversion of the nitro group to an amine can be accomplished by methods known to one skilled in the art such as by reduction including by hydrogenation, such as with catalytic hydrogenation including treatment with hydrogen in the presence of a transition metal catalyst, e.g. Pt or sulfided Pt supported on carbon or alumina, Pd supported on carbon, barium sulfate, calcium carbonate or Raney sponge nickel. In certain embodiments of this step of the process, catalysts include 10% Pd/C.

In certain embodiments of this step of the process, the hydrogenation occurs in the presence of a solvent, such as an alcohol, e.g. MeOH or EtOH, cyclic ethers, e.g. THF, and EtOAc.

Alternatively, reduction of the nitro compound with iron powder, preferably at a temperature above about $50°$ C., and more preferably at about $80°$ C., yields the amine. Alternatively one can use 10% Pd/C in the presence of an excess of $NH_4CO_2H$. Alternatively, reduction of the nitro compound, such as with acid, for example AcOH, and zinc yields the amine.

The reaction mixtures and solid samples are analyzed on an Agilent HPLC system using a Waters Symmetry $C_{18}$ (150× 4.6 cm) column with the detector set at 254 nm. The gradient eluting solvent mixture is water and MeOH containing 0.1% of TFA and starting from 90% aqueous MeOH to 60% aqueous MeOH over 15 min and then increased to 65% aqueous MeOH over the next 5 minutes at a flow rate of 1.0 mL/min.

The present invention is further defined in the following Examples, in which all parts and percentages are by weight and area percent (A %) and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

| Abbreviations | |
|---|---|
| IPAC | isopropyl acetate |
| IPA | isopropyl alcohol |
| ACN | acetonitrile |
| NaOH | sodium hydroxide |
| Et$_3$N, TEA | triethylamine |
| HCl | hydrochloric acid |
| Pd/C | palladium/carbon |
| THF | tetrahydrofuran |
| H$_2$ | hydrogen |
| H$_2$SO$_4$ | sulfuric acid |
| HNO$_3$ | nitric acid |
| MSA, MeSO$_3$H, MsOH | methanesulfonic acid |
| DCM | dichloromethane, methylene chloride |

-continued

Abbreviations

| | |
|---|---|
| TFA | trifluoroacetic acid |
| F$_2$HCCOOH | difluoroacetic acid |
| PPA | phosphoric acid |
| HI | hydrogen iodide |
| HBr | hydrogen bromide |
| AcOH | acetic acid |
| ZnCl2 | zinc chloride |
| ZnBr$_2$ | zinc bromide |
| TiCl$_4$ | titanium tetrachloride |
| SnCl$_2$ | stannous chloride |
| CuCl | cuprous chloride |
| CuBr | cuprous bromide |
| PCl$_3$ | phosphorous trichloride |
| A% | area percent |
| MeOH | methanol |
| EtOH | ethanol |
| DIEA | di-isopropylethylamine |
| DMAP | 4-dimethylaminopyridine |
| RT | room temperature |
| DMF | dimethylformamide |
| DMAC | dimethylacetamide |
| EtOAc | ethyl acetate |
| NH$_4$CO$_2$H | ammonium formate |
| BMImHSO$_4$ | 1-butyl-3-methyl-imidazolium hydrogen sulphate |
| BMImH$_2$PO$_4$ | 1-butyl-3-methyl-imidazolium dihydrogen phosphate |
| HMImTA | 1-methylimidazolium hydrogen trifluoracetate |
| HMImBF$_4$ | 1-methylimidazolium hydrogen boron tetrafluoride |
| HMImNO$_3$ | 1-methylimidazolium hydrogen nitrate |
| HMImOTf | 1-methylimidazolium hydrogen triflate |

Example 1

Preparation of 3,3-dimethyl-3H-indole [the Fischer indole reaction]

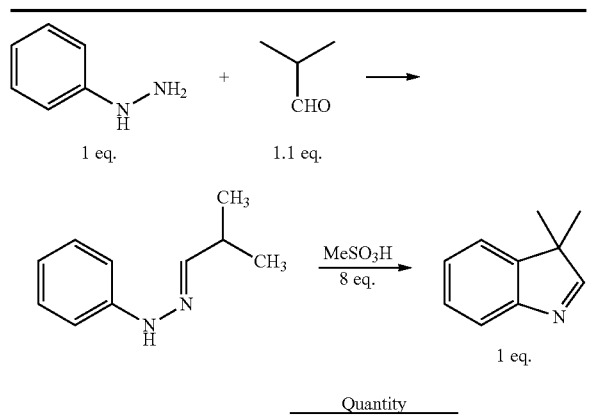

| Material/CAS# | MW | Amount | Unit | Mol | Equiv |
|---|---|---|---|---|---|
| phenylhydrazine/ 100-63-0 | 108.14 | 200 | g | 1.85 | 1.0 |
| isobutyraldehyde/ 75-79-2 | 72.11 | 146.7 | g | 2.04 | 1.1 |
| Methanesulfonic acid/ 78-84-2 | 96.1 | 1.422 | kg | 14.8 | 8.0 |
| Heptane/ 142-82-5 | 114 | 600 | mL | | |

*Based on the assay of the indoline.

Phenylhydrazine (200 g) and heptane (600 mL) were charged to a 2 L dry RB-flask under nitrogen at 10-12° C., and the vessel was degassed three times with nitrogen/vacuum, followed by the addition of isobutyraldehyde (146.7 g) dropwise at temperature<20° C. The resulting mixture was stirred for 1 h at 18-20° C. or until 99 A % conversion. To a 5 L reactor, MSA (1.422 kg) was charged followed by slow addition of the reaction mixture prepared in the 2 L RB-flask. The reaction mixture was stirred overnight at 18-20° C. to afford a crude mixture of 3,3-dimethyl-3H-indole. (<2 A % for the starting material, Assay: 91% yield).

The following Fischer indole reaction studies (Example 1A-1S) were prepared by the method described above, unless changes in solvents, acids and temperatures which are specifically described. For examples 1A-1D, 1J-1K and 1O-1S, the hydrazone was generated in situ.

A: TFA/DCM/35° C.: The same procedure as the above Fischer indole reaction, phenylhydrazine (5.41 g), 400 mL DCM, isobutyraldehyde (4.69 g), TFA (11.5 mL), 17 h at 35° C., only 5 A % desired product.

B: TFA/ACN/35° C.: The same procedure as the above Fischer indole reaction, phenylhydrazine (5.41 g), 50 mL ACN, isobutyraldehyde (4.69 g), TFA (11.5 mL), 17 h at 35° C., only 15 A % desired product.

C: TFA/THF/35° C.: The same procedure as the above Fischer indole reaction, phenylhydrazine (5.41 g), 50 mL ACN, isobutyraldehyde (4.69 g), TFA (11.5 mL), 17 h at 35° C., only 10 A % desired product.

D: AcOH/60° C.: The same procedure as the above Fischer indole reaction, phenylhydrazine (5.40 g), isobutyraldehyde (3.97 g), AcOH (9 g), 17 h at 60° C., only 57 A % desired product.

J: MSA/toluene/20° C.: The same procedure as the above Fischer indole reaction, phenylhydrazine (2.16 g), isobutyraldehyde (1.59 g), 40 mL toluene and MSA (5.77 g), 17 h at 20° C., there is 90 A % desired product.

K: MSA/heptane/20° C.: The same procedure as the above Fischer indole reaction, phenylhydrazine (8.64 g), isobutyraldehyde (6.36 g), 24 mL heptane and MSA (38.4 g), 2 days at 20° C., there is 92 A % desired product.

O: TFA/DCM/25° C.: The same procedure as the above Fischer indole reaction, phenylhydrazine (2.163 g), 50 mL DCM, isobutyraldehyde (1.59 g), TFA (4.62 mL), 17 h at rt, provided <1 A % desired product.

P: Formic Acid/THF/20° C.: The same procedure as the above Fischer indole reaction, phenylhydrazine (2.163 g), isobutyraldehyde (1.59 g), 40 mL THF and formic acid (2.76 g, 3 g Sieve), 17 h at 20° C., 2 h at 35° C., there is 3 A % desired product.

Q: MSA/heptane/25° C.: The same procedure as the above Fischer indole reaction, phenylhydrazine (100 g), 300 mL heptane, isobutyraldehyde (73.35 g), MSA (711.14 g), 17 h at 18-25° C., 91 A % desired product.

R: MSA/heptane/30° C.: The same procedure as the above Fischer indole reaction, phenylhydrazine (4.32 g), 12 mL heptane, isobutyraldehyde (3.18 g), MSA (19.2 g), 17 h at 30° C., 85 A % desired product.

S: TFA/60° C.: The same procedure as the above Fischer indole reaction, phenylhydrazine (5.40 g), isobutyraldehyde (3.97 g), TFA (17 g), 17 h at 60° C. provided <1 A % desired product.

Example 2

Preparation of Hydrazone

Phenylhydrazine (21.64 g), 10 g of molecular sieve and THF (100 ml) were charged to a 240 mL dry RB-flask under nitrogen at 0-5° C., and the vessel was then degassed three times with nitrogen/vacuum, followed by the addition of isobutylaldehyde (15.86 g). The resulting reaction mixture was stirred for 0.5 h (99 A % conversion). The sieve was filtered off and the THF was removed under vacuum to afford the hydrazone as an oil (38 g).

For examples 1E-1I and 1L-1N, the cyclization was performed on isolated hydrazone from Example 2 directly.

E: TFA/IPAC/40° C.: The same procedure as the above Fischer indole reaction, phenylhydrazone (1.62 g), 20 mL IPAC, TFA (3.42 g), 17 h at 40° C. provided <1 A % desired product.

F: H₂SO₄/THF/40° C.: The same procedure as the above Fischer indole reaction, phenylhydrazone (1.62 g), 15 mL THF and 50% H₂SO₄ (2.94 g), 3 h at 40° C., there is 40 A % desired product.

G: p-Toluenesulfonic acid/THF/40° C.: The same procedure as the above Fischer indole reaction, phenylhydrazone (1.62 g), 15 mL THF and p-toluenesulfonic acid (5.7 g), 3 h at 40° C., there is 58 A % desired product.

H: MSA/THF/40° C.: The same procedure as the above Fischer indole reaction, phenylhydrazone (1.62 g), 15 mL THF and MSA (1.45 g), 3 h at 40° C., there is 60 A % desired product.

I: F₂CHCOOH/THF/40° C.: The same procedure as the above Fischer indole reaction, phenylhydrazone (1.62 g), 15 mL THF and F₂CHCOOH (1.44 g), 3 h at 40° C., there is 20 A % desired product.

L: AcOH/40° C.: The same procedure as the above Fischer indole reaction, phenylhydrazone (1.62 g), AcOH (5 mL), 1 h at T, 24 h at 40° C., provided 20 A % desired product.

M: Formic acid/70° C.: The same procedure as the above Fischer indole reaction, phenylhydrazone (1.62 g), formic acid (5 mL), 17 h at 70° C. provided <1 A % desired product.

N: TFA/Toluene/48° C.: The same procedure as the above Fischer indole reaction, phenylhydrazone (1.62 g), 20 mL toluene, TFA (3.42 g), 17 h at 48° C. provided <1 A % desired product.

TABLE 1

| # | Solvent | Catalyst | Temp ° C. | A % Yield |
|---|---------|----------|-----------|-----------|
| 1 | heptane | MSA | 20 | 98 |
| 1A | DCM | TFA | 35 | 5 |
| 1B | ACN | TFA | 35 | 15 |
| 1C | THF | TFA | 35 | 10 |
| 1D | none | AcOH | 60 | 57 |
| 1E | IPAC | TFA | 40 | <1 |
| 1F | THF | H₂SO₄ | 40 | 40 |
| 1G | THF | p-Toluenesulfonic acid | 40 | 58 |
| 1H | THF | MSA | 40 | 60 |
| 1I | THF | F₂CHCOOH | 40 | 20 |
| 1J | toluene | MSA | 20 | 90 |
| 1K | heptane | MSA | 20 | 92 |
| 1L. | none | AcOH | 40 | 20 |
| 1M. | none | Formic acid | 70 | <1 |
| 1N | toluene | TFA | 48 | <1 |
| 1O | DCM | TFA | rt | <1 |
| 1P. | THF | Formic acid | 20/35 | 3 |
| 1Q | heptane | MSA | 25 | 91 |
| 1R | heptane | MSA | 30 | 85 |
| 1S | none | TFA | 60 | <1 |

Example 3

Preparation of 3,3-dimethylindoline HCl salt

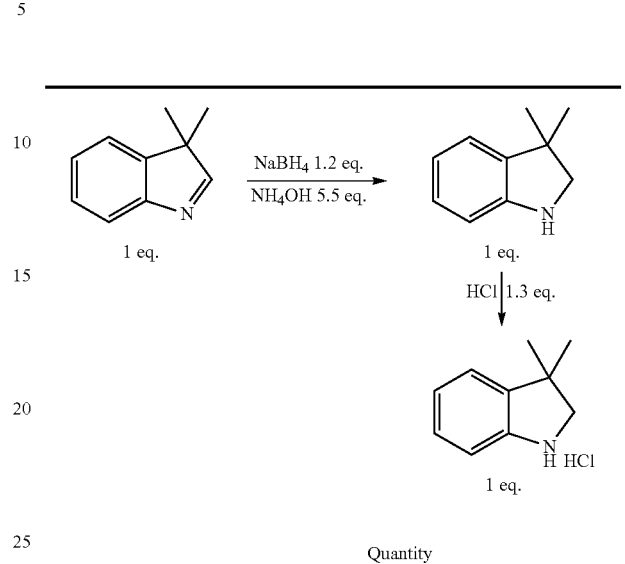

| Material/CAS# | MW | Amount | Unit | Mol | Equiv |
|---|---|---|---|---|---|
| 3,3-dimethyl-3H-indole | | | | | |
| Sodium borohydride/16940-66-2 | 37.83 | 84 | g | 2.22 | 1.2 |
| Ammonium hydroxide/1336-21-6 | 35.05 | 943 | mL | 15.7 | 8.5 |
| IPAC/110-19-0 | 116.16 | 600 | mL | | |
| Heptane/142-82-5 | 114 | 800 | mL | | |
| 5 N HCl/IPA/7647-01- | 36.5 | 364 | mL | 1.85 | 1.3* |
| IPA/67-63-0 | 62.11 | 236 | mL | | |
| D I water | 18 | 1.18 | L | | |
| Brine | 58.5 | 80 | mL | | |

The resulting mixture from Example 1 was treated with a slow addition of a solution of NaBH₄ (84 g) in 400 mL DI basified with 5N NaOH (pH~13) water in 3 h at a temperature below 10° C., then warmed to about room temperature. The reaction was worked up by adjusting pH to 8 with 14.5N NH₄OH and the phases were then separated. The aqueous phase was extracted with IPAC (300 mL×2). The combined organic phase was washed with DI water (80 mL) and saturated brine (80 mL) to give the corresponding indoline solution (containing 231 g of 3,3-dimethylindoline, 85% assay yield.)

To this indoline solution (in heptane/IPAC) was added 194 mL propan-2-ol, followed by the addition of 5 N HCl in IPA (408 mL) to form a suspension, which was stirred for 2 h before filtration. The wet cake was then washed with heptane (100 mL×2) to afford the 3,3-dimethylindoline HCl salt. (255.6 g, 75.5% yield, 98.4 A % for the HCl salt).

Example 4

Preparation of 3,3-dimethyl-6-nitroindoline

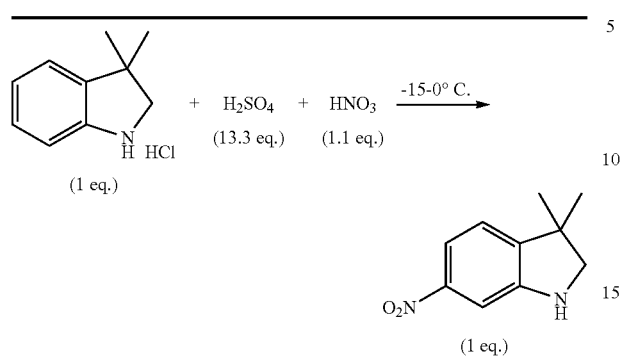

| Material/CAS# | MW | Quantity Amount | Unit | Mol | Equiv |
|---|---|---|---|---|---|
| 3,3-dimethylindoline HCl | 183.7 | 200 | g | 1.089 | 1.0 |
| H₂SO₄/7664-93-9 | 98 | 1419 | g | 14.48 | 13.3 |
| HNO₃/7697-37-2 | 63 | 75.6 | g | 1.20 | 1.1 |
| IPAC/110-19-0 | 116.16 | 800 | mL | | |
| Ammonium hydroxide/ 1336-21-6 | 35.05 | 2184 | mL | 31.66 | 29.1 |
| D.I. Water | 18 | 600 | mL | | |
| Brine | 58.5 | 400 | mL | | |

H₂SO₄ (1.42 kg) and 3,3-dimethylindoline HCl salt (Example 3, 200 g) were charged to a dry 5 L RB-flask under nitrogen at 20-25° C. The reaction mixture was cooled to −15 to 10° C. A solution of HNO₃ (75.6 g) in water (18.89 g) was added drop-wise. The resulting reaction mixture was stirred for 1 h. The mixture was transferred into a mixture of 2.084 L of 30% NH₄OH and 600 mL of water at 0-5° C. The pH was adjusted to 8-9 with NH₄OH, and after the addition of 800 mL of IPAC, phases were separated. The aqueous phase was extracted with IPAC (400 mL). The combined organic phase was washed with saturated brine (400 mL) to give a solution of 3,3-dimethyl-6-nitroindoline. (190.5 g, 91%, 94 A %).

Example 5

Preparation of 1-(3,3-dimethyl-6-nitroindoline-1y)ethanone

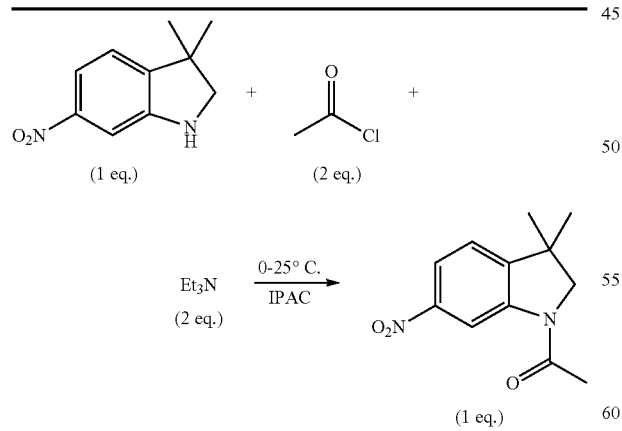

| Material/CAS# | MW | Quantity Amount | Unit | Mol | Equiv |
|---|---|---|---|---|---|
| 3,3-dimethyl-6-nitroindoline | 192.2 | 190 | g | 0.99 | 1.0 |
| Acetyl chloride/75-36-5 | 78.5 | 155.6 | g | 1.98 | 2 |

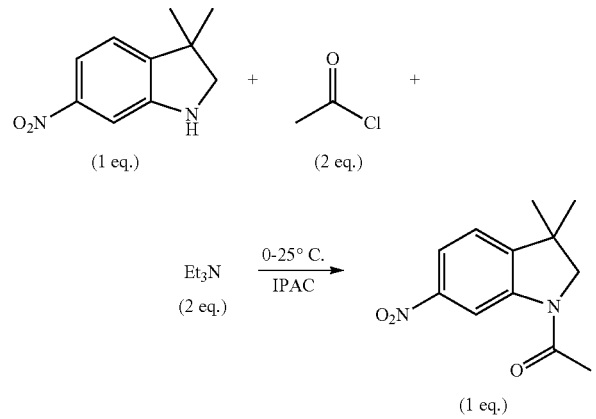

| Material/CAS# | MW | Quantity Amount | Unit | Mol | Equiv |
|---|---|---|---|---|---|
| Et₃N/121-44-8 | 101.2 | 200.6 | g | 1.98 | 2 |
| IPAC/110-19-0 | 116.16 | 1200 | mL | | |
| Heptane/142-82-5 | | 200 | mL | | |
| DI water | | 1600 | mL | | |

A solution of 3,3-dimethyl-6-nitroindoline (Example 4, 190.5 g) in 1200 mL IPAC, Et₃N (200.6 g) was charged to a 1-L jacketed reactor, followed by the drop-wise addition of acetyl chloride (155.4 g) while maintaining reaction temperature<25° C. The reaction contents were stirred for 1 h at 20-25° C. 1200 mL D.I. water was charged slowly at T<30° C. to form a suspension. The product was isolated by filtration. Wet cake was washed with D.I. water (200 mL×2) and heptane (200 mL), and was dried at 50° C. under vacuum until constant weight. (193 g, 83.2 wt % adjusted yield, 99.15 A %, 99.5 wt % (dry))

Example 6

Preparation of 1-(6-amino-3,3-dimethyl-indolin-1-1y)ethanone

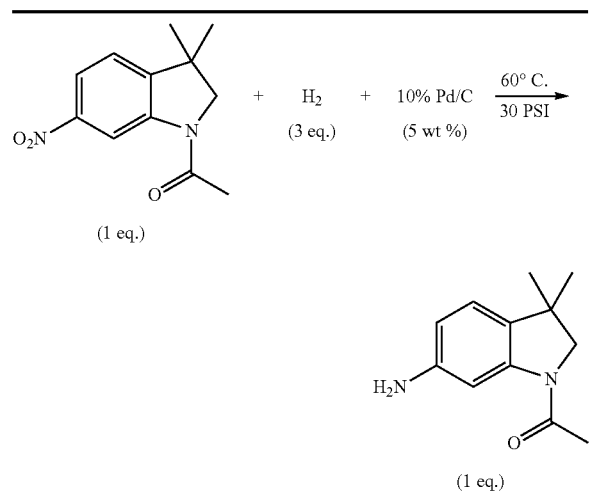

| Material/CAS# | MW | Quantity Amount | Unit | Mol | Equiv |
|---|---|---|---|---|---|
| 1-(3,3-dimethyl-6-nitro-indolin-1-yl)ethanone | 234.2 | 50 | g | 213.5 | 1.0 |

-continued

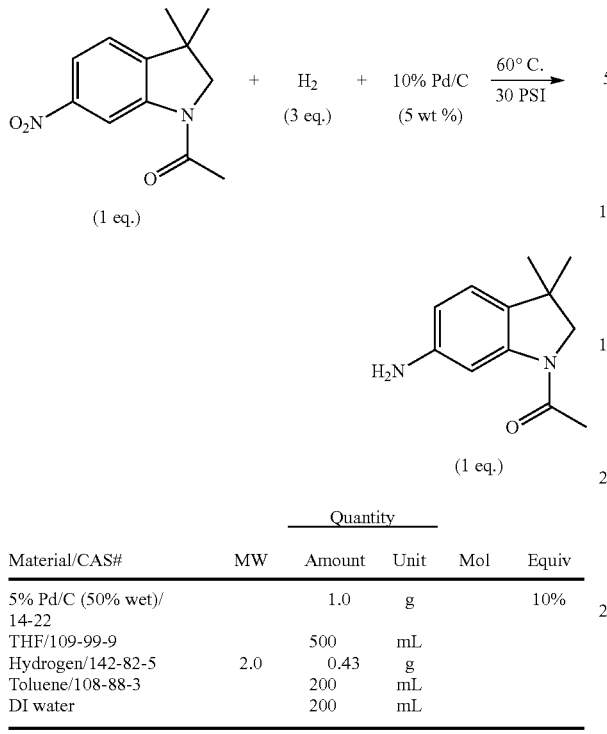

| Material/CAS# | MW | Quantity Amount | Unit | Mol | Equiv |
|---|---|---|---|---|---|
| 5% Pd/C (50% wet)/14-22 | | 1.0 | g | | 10% |
| THF/109-99-9 | | 500 | mL | | |
| Hydrogen/142-82-5 | 2.0 | | | 0.43 | g |
| Toluene/108-88-3 | | 200 | mL | | |
| DI water | | 200 | mL | | |

1-(3,3-Dimethyl-6-nitroindoline-1y)ethanone (Example 5, 50 g), 5% Pd/C (1 g, 50% wet) and THF (200 mL) were charged to a 400 mL hydrogenation reactor. The slurry was degassed with vacuum/hydrogen three times and stirred for 6 h at 60° C. under hydrogen (30 PSI). The resulting mixture was filtered through a thin layer of Celite™ and the cake was washed with THF (150 mL×2). The filtrate and washes were combined and concentrated in vacuo, followed by addition of toluene (150 mL). The product was isolated by filtration and the wet cake was washed with D.I. water (100 mL×2) and 50 mL toluene to afford 1-(6-amino-3,3-dimethyl-indolin-1-yl)ethanone (38.5 g, 94% yield, >99.9 A %, 100 wt %).

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in their entireties.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A process for the formation of

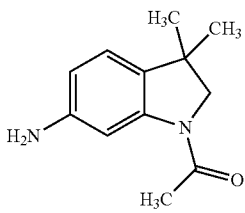

comprising a) reacting

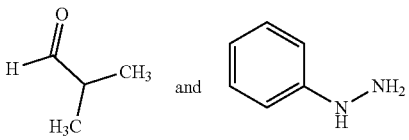

to form a hydrazone;

b) cyclization of the hydrazone in the presence of a Fischer catalyst to form a 3H-indole;

c) reduction of the 3H-indole to form a 2,3-dihydro-indole;

d) nitration of the 2,3-dihydro-indole to form a 6-nitro-2,3-dihydro-indole;

e) acylation of the 6-nitro-2,3-dihydro-indole to form the protected 6-nitro-2,3-dihydroindole; and f) conversion of the nitro group to form 6-amino-2,3-dihydro-indole.

2. The process of claim 1 wherein the Fischer indole catalyst is methanesulfonic acid.

3. The process of claim 1 wherein the Fischer indole catalyst comprises at least one equivalent of methanesulfonic acid.

4. The process of claim 3 wherein the cyclization is at a temperature of between −15° C. and about 30° C.

5. The process of claim 1 wherein the cyclization is at a temperature of about 20° C.

6. The process of claim 1 wherein the cyclization comprises a solvent selected from heptane, hexane, toluene, benzene and xylenes.

7. The process of claim 1 wherein the reduction comprises treatment with sodium cyanoborohydride or sodium borohydride.

8. The process of claim 1 wherein the reduction is at a temperature of about room temperature.

9. The process of claim 1 wherein the nitration comprises treatment with $HNO_3$ and sulfuric acid.

10. The process of claim 1 wherein acylation comprises treatment with acetyl chloride.

11. The process of claim 1 wherein the reduction of the nitro group comprises hydrogenation.

12. The process of claim 6 wherein the solvent is heptane.

13. The process of claim 1 comprising cyclization of (E)-1-(2-methylpropylidene)-2-phenylhydrazine in the presence of methanesulfonic acid.

14. The process of claim 13 comprising at least one equivalent of methanesulfonic acid.

15. The process of claim 13 wherein the temperature is between −15° C. and about 30° C.

16. The process of claim 13 wherein the temperature is about 20° C.

17. The process of claim 13 comprising a solvent selected from heptane, hexane, toluene, benzene and xylenes.

18. The process of claim 17 wherein the solvent is heptane.

19. The process of claim 13 comprising at least five equivalents of methanesulfonic acid.

* * * * *